United States Patent [19]

Effland et al.

[11] Patent Number: 5,179,204

[45] Date of Patent: Jan. 12, 1993

[54] N-SUBSTITUTED-4-PYRIMIDINAMINES AND PYRIMIDINEDIAMINES

[75] Inventors: Richard C. Effland; Joseph T. Klein, both of Bridgewater; Larry Davis, Sergeantsville; Gordon E. Olsen, Somerset, all of N.J.

[73] Assignee: Hoechst-Roussel Pharmaceuticals Incorporated, Somerville, N.J.

[21] Appl. No.: 584,554

[22] Filed: Sep. 18, 1990

Related U.S. Application Data

[62] Division of Ser. No. 402,415, Sep. 5, 1989, Pat. No. 4,983,608.

[51] Int. Cl.$^5$ .......................................... C07D 401/12
[52] U.S. Cl. ................................. 544/328; 544/319; 544/326; 544/333
[58] Field of Search ................ 544/319, 326, 328, 333

[56] References Cited

FOREIGN PATENT DOCUMENTS 0772195 3/1972 Belgium ............................. 544/328

Primary Examiner—Mukund J. Shah
Assistant Examiner—Y. N. Gupta
Attorney, Agent, or Firm—Elliott Korsen

[57] ABSTRACT

This invention relates to N-heteroaryl-4-pyrimidinamines of the formula

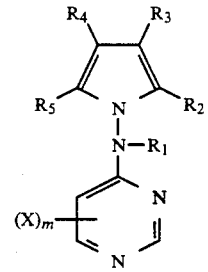

where $R_1$ is hydrogen, loweralkyl, aryl, or arylloweralkyl; $R_2$ and $R_3$ are independently hydrogen or loweralkyl, or $R_2$ and $R_3$ taken together are aryl; $R_4$ and $R_5$ are independently hydrogen or loweralkyl, or $R_4$ and $R_5$ taken together are aryl; X is hydrogen, halogen, cyano, nitro, amino, loweralkyl, loweralkoxy, trifluoromethyl or

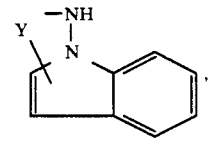

where Y is hydrogen, halogen or loweralkyl; m is an integer of 1 to 3; and the pharmaceutically acceptable acid addition salts thereof and where applicable the geometrical and optical isomers and racemic mixtures thereof. The compounds of this invention display utility as memory enhancing agents and as analgesic agents.

2 Claims, No Drawings

N-SUBSTITUTED-4-PYRIMIDINAMINES AND PYRIMIDINEDIAMINES

This is a division of application Ser. No. 402,415 filed Sep. 5, 1989, now U.S. Pat. No. 4,983,608.

This invention relates to compounds of the formula (I)

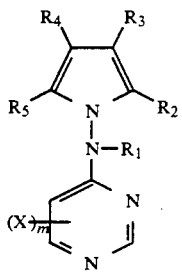

where $R_1$ is hydrogen, loweralkyl, aryl, or arylloweralkyl; $R_2$ and $R_3$ are independently hydrogen or loweralkyl, or $R_2$ and $R_3$ taken together are aryl; $R_4$ and $R_5$ are independently hydrogen or loweralkyl, or $R_4$ and $R_5$ taken together are aryl; X is hydrogen, halogen, cyano, nitro, amino, loweralkyl, loweralkoxy, trifluoromethyl or

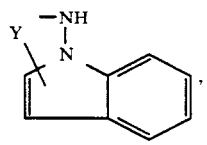

where Y is hydrogen, halogen or loweralkyl; m is an integer of 1 to 3; and the pharmaceutically acceptable acid addition salts thereof and where applicable the geometrical and optical isomers and racemic mixtures thereof. The compounds of this invention display utility as memory enhancing agents and as analgesic agents.

Throughout the specification and appended claims, a given chemical formula or name shall encompass all optical and geometrical isomers and racemic mixtures, where such isomers and mixtures exist.

In the above definition, the term "lower" means the group it is describing contains from 1 to 6 carbon atoms. The term "alkyl" refers to a straight or branched chain hydrocarbon containing no unsaturation, e.g. methyl, ethyl, propyl, isopropyl, 2-butyl, n-butyl, t-butyl and straight and branched chain pentyl and hexyl. The term "arylloweralkyl" refers to a monovalent substituent which consists of an "aryl" group, e.g. phenyl, o-tolyl, m-methoxyphenyl, etc., as defined by the formula

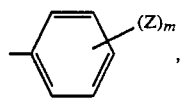

where Z is as defined below and m is an integer of 1 to 3, linked through a loweralkylene group having its free valence bond from a carbon of the loweralkylene group, and having a formula of -loweralkylene where Z is hydrogen, halogen, loweralkyl, loweralkoxy, trifluoromethyl, nitro and amino; the term "alkylene" refers to a bivalent radical of the lower branched or unbranched alkyl group it is derived from having valence bonds from two terminal carbons thereof, e.g., ethylene, propylene, isopropylene, etc.; the term "alkoxy" refers to a monovalent substituent which consists of an alkyl group linked through an ether oxygen having its free valence bond from the ether oxygen, e.g. methoxy, ethoxy, propoxy, hexoxy, etc., and the term "halogen" refers to a member of the halogen family consisting of fluorine, chlorine, bromine and iodine.

The compounds of the present invention are prepared in the following manner. Throughout the description of the synthetic steps, X, Y, $R_1$, $R_2$, $R_3$, $R_4$ and $R_5$ and the integer m shall have the respective meanings given above unless otherwise stated or indicated.

A substituted pyrimidine of formula II

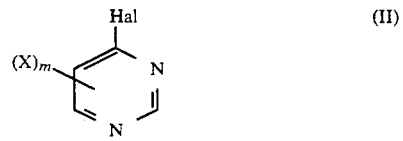

where Hal is a halogen, is reacted with a compound of formula III

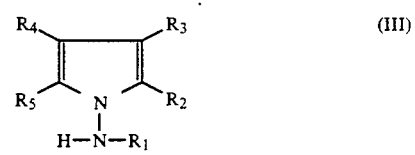

in a typical nucleophilic type reaction to afford a compound of formula I.

Compounds II and III are well known or can be easily synthesized utilizing procedures well known in the art. For example, the procedures described in Bredereck et al., *Chem. Ber.*, 98, 3883 (1965) and Bredereck et al., *Chem. Ber.*, 100, 3664 (1967) are utilized to synthesize the substituted pyrimidines (II). Typically the reaction of Compound II and Compound III is conducted in a solvent, e.g., a loweralkanol such as ethanol, methanol, propanol, isopropanol or 1-methyl-2-pyrrolidinone, in the presence of a base such as triethylamine. The reaction is typically carried out at a temperature of about 60° C. to 150° C. for 1 to 30 hours.

The compounds of formula I where X is hydrogen are prepared by catalytic hydrogenation of the 6-Cl compound with hydrogen gas, some magnesium oxide and a suitable catalyst such as a noble metal catalyst. Noble metal catalysts include palladium, platinum or rhodium, etc. The preferred is palladium on charcoal. Said hydrogenation is typically carried out under 1 atmosphere pressure in the presence of a suitable solvent such as isopropanol, ethanol or methanol at a temperature of 20° C. to 30° C. for 1 to 10 hours.

In another embodiment, one mole of compound II, where X is halogen, is reacted with at least two moles of compound III, to form compound IV of the formula

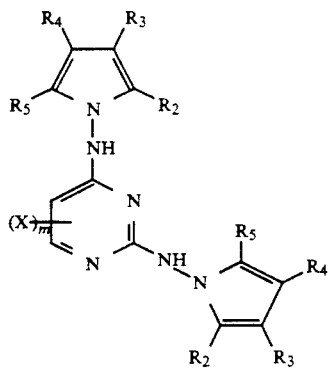

(IV)

Typically, this reaction is carried out in a polar solvent, e.g. 1-methyl-2-pyrrolidinone, ethanol, isopropanol, etc. at a temperature of 60° to 150° C. for 1 to 30 hours.

The N-substituted-4-pyrimidinamines and pyrimidinediamines of the present invention are useful as analgesic agents due to their ability to alleviate pain in mammals which is demonstrated in the phenyl-paraquinone writhing assay in mice, a standard assay for analgesia [Proc. Soc. Exptl. Biol. Med., 95, 729 (1957)]. Presented in Table I is the analgesic effect of some of the compounds of the invention, expressed as the percent decrease in writhing at a given dose (20 mg/kg s.c.).

TABLE I

| COMPOUND | Analgesic Activity % Inhibition of Writhing at a Screening Dose of 20 mg/kg s.c. |
|---|---|
| 6-Chloro-N-(1H-pyrrol-1-yl)-4-pyrimidinamine | 39 |
| 6-Chloro-N-methyl-N-(1H-pyrrol-1-yl)-4-pyrimidinamine | 42 |
| N-(1H-pyrrol-1-yl)-4-pyrimidinamine | 30 |
| 2-Chloro-N-methyl-N-(1H-pyrrol-1-yl)-4-pyrimidinamine | 38 |
| 6-Chloro-N-propyl-N-(1H-pyrrol-1-yl)-4-pyrimidinamine | 46 |
| N-(1H-indol-1-yl)-N-propyl-4-pyrimidinamine | 58 |
| 6-Chloro-N-(1H-indol-1-yl)-N-propyl-4-pyrimidinamine | 40 |
| 6-Chloro-N-(3-methyl-1H-indol-1-yl)-4-pyrimidinamine | 45 |
| N,N'-bis(3-methyl-1H-indol-1-yl)-4,6-pyrimidindiamine | 33 |
| 6-Chloro-N-(3-methyl-1H-indol-1-yl)-N-propyl-4-pyrimidinamine | 36 |
| N-(3-methyl-1H-indol-1-yl)-N-propyl-4-pyrimidinamine | 60 |
| 5-Cyano-N-(1H-indol-1-yl)-4-pyrimidinamine | 44 |
| N-(pyrimidin-4-yl)-9H-carbazol-9-amine | 65 |
| 5-Cyano-N-(1H-indol-1-yl)-N-propyl-4-pyrimidinamine | 75 |
| Propoxyphene (standard) | 50* |

*3.9 mg/kg s.c.

The analgesic relief of pain is achieved when the N-substituted-4-pyrimidinamines and pyrimidinediamines are administered to a subject requiring such treatment as an effective oral, parenteral or intravenous dose of from 0.1 to 25 mg/kg of body weight per day. A particularly effective amount is about 10 mg/kg of body weight per day. It is to be understood that for any particular subject specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The N-substituted-4-pyrimidinamines and pyrimidinediamines of the present invention are also useful in the treatment of various memory dysfunctions such as Alzheimer's disease. This utility is demonstrated by the ability of these compounds to restore cholinergically deficient memory in the Dark Avoidance Assay, where they are, in general, active over a broader dose range than heretofore known compounds, a distinct therapeutic advantage.

Dark Avoidance Assay

In this assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

| Compound | Dose mg/kg s.c. by Body Weight | % of Animals with Scopolamine Induced Memory Deficit Reversed |
|---|---|---|
| N-(1H-indol-1-yl)-N-propyl-4-pyrimidinamine | 1.25 | 27 |
| 6-Chloro-N-(1H-indol-1-yl)-N-propyl-4-pyrimidinamine | 1.25 | 47 |
| 6-Chloro-N-(3-methyl-1H-indol-1-yl)-4-pyrimidinamine | 1.25 | 33 |
| N-(3-methyl-1H-indol-1-yl)-4-pyrimidinamine | 1.25 | 20 |
| 5-Cyano-N-(1H-indol-1-yl)-4-pyrimidinamine | 1.25 | 27 |
| Pilocarpine (standard) | 5.00 | 23 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for the purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 to 300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel TM, cornstarch and the like; a lubricant such as magnesium stearate or Sterotex TM; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and contain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following compounds: a sterile diluent such as water for injection, saline solution, fixed oils, polyethylene glycols, glycerine, propylene glycol or other synthetic solvents, antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
6-Chloro-N-benzyl-N-(1H-indol-1-yl)-4-pyrimidinamine;
N-Benzyl-N-(1H-indol-1-yl)-4-pyrimidinamine;
6-Methoxy-N-(1H-indol-1-yl)-N-propyl-4-pyrimidinamine;
6-Chloro-2-methyl-N-(1H-indol-1-yl)-4-pyrimidinamine;
2-Methyl-N-(1H-indol-1-yl)-4-pyrimidinamine;
2-Chloro-6-methyl-N-(3-methyl-1H-indol-1-yl)-4-pyrimidinamine;
N-(1H-Indol-1-yl)-N-(4-nitrophenyl)-4-pyrimidinamine.

The following examples are given for illustrative purposes and are not to be considered as limiting the invention disclosed herein.

EXAMPLE 1

6-Chloro-N-(1H-pyrrol-1-yl)-4-pyrimidinamine

To a solution of 4,6-dichloropyrimidine (5.8 g) in 40 ml of ethanol was added triethylamine (10 ml), and then 1-aminopyrrole (3.2 g) in 40 ml of ethanol. This mixture was heated to 80° C. and stirred for 22 hours. The mixture was cooled, poured into water, extracted with ethyl acetate, washed with water and dried (saturated sodium chloride solution, anhydrous magnesium sulfate).

After filtering, the solvent was evaporated to yield a solid (7.5 g) which was preabsorbed on silica gel and eluted with 5% ethyl acetate/dichloromethane (DCM hereafter) via flash chromatography. The desired fractions were evaporated to yield a solid (3.5 g). This solid was recrystallized from ether to yield 2.0 g (27.0%) of 6-Chloro-N-(1H-pyrrol-1-yl)-4-pyrimidinamine, m.p. 196°–198° C.

Analysis: Calculated for $C_8H_7ClN_4$: 49.37%C, 3.63%H, 28.79%N. Found: 49.37%C, 3.62%H, 28.80%N.

EXAMPLE 2 a. N-Methyl-1H-pyrrol-1-amine

To a solution of N-(1H-pyrrol-1-yl) carbamic acid ethyl ester (9.0 g) in 30 ml tetrahydrofuran (THF) at 5° C., was added potassium t-butoxide (7.8 g) and the mixture was stirred at 5° C. for one hour. To this was added methyl iodide (4.1 ml) in ten minutes, and the mixture stirred at 5° C. for one hour, then at ambient temperature for four hours. The mixture was poured into 100 ml ice water, stirred for five minutes, then extracted with ethyl acetate. The organic layer was washed with water, then dried (saturated NaCl, anhydrous $MgSO_4$). After filtering, the solvent was evaporated to an oil, 9.4 g (93%), of N-methyl-N-(1H-pyrrol-1-yl) carbamic acid ethyl ester. To a solution of N-methyl-N-(1-H-pyrrol-1-yl) carbamic acid ethyl ester (9.4 g) in 15 ml ethylene glycol, was added a solution of NaOH (5 g) in 10 ml water. After stirring at 120° C. for four hours, the mixture was poured into 100 ml ice water, stirred for five minutes, then extracted with ethyl acetate. The organic layer was washed with water, then dried (saturated NaCl, anhydrous $MgSO_4$), filtered and then evaporated to an oil which was vacuum distilled to give N-methyl-1H-pyrrol-1-amine 4.3 g (81%), b.p. 32°–5° C.

b.
6-Chloro-N-methyl-N-(1H-pyrrol-1-yl)-4-pyrimidinamine

To a solution of 4,6-dichloropyrimidine (5.0 g), in 50 ml absolute ethanol was added triethylamine (5.8 ml), followed by a solution of N-methyl-1H-pyrrol-1-amine (3.2 g), in 30 ml ethanol. After stirring at 80° C. for twenty hours, the mixture was poured into 300 ml water, stirred for five minutes, and the resultant tan precipitate collected and dried to give 2.4 g, m.p. 88°-89° C. This material was sublimed at 75° C./1.0 mm Hg to give 2.2 g (31%) of 6-Chloro-N-methyl-N-(1H-pyrrol-1-yl)-4-pyrimidinamine, m.p. 88°-89° C.

Analysis: Calculated for $C_9H_9ClN_4$: 51.81%C, 4.35%H, 26.85%N. Found: 51.86%C, 4.38%H, 26.95%N.

EXAMPLE 3

N-(1H-Pyrrol-1-yl)-4-pyrimidinamine

To a slurry of 10% Pd/C (1.0 g) and MgO (0.8 g) in 15 ml of ethanol was added 6-chloro-N-(1H-pyrrol-1-yl)-4-pyrimidinamine (3.5 g), in 135 ml of ethanol and this mixture was hydrogenated under atmospheric pressure at room temperature. When the reduction was complete, the mixture was filtered through celite and the filtrate evaporated to yield a solid (5.9 g). This material was eluted with ethyl acetate on a silica gel column via flash chromatography. The desired fractions were evaporated to yield a solid (2.28 g) which was sublimed to yield 1.9 g (66%) of N-(1H-pyrrol-1-yl)-4-pyrimidinamine, m.p. 134°-136° C.

Analysis: Calculated for $C_8H_8N_4$: 59.99%C, 5.03%H, 34.98%N. Found: 59.82%C, 4.92%H, 34.83%N.

EXAMPLE 4

6-Chloro-$N^4$-(1H-pyrrol-1-yl)-4,5-pyrimidinediamine

A solution of 4,6-dichloro-5-pyrimidinamine (5 g) and 1H-pyrrol-1-amine (12 g), in 150 ml isopropanol with 2 ml ether-HCl was stirred five hours at reflux then was cooled, filtered and evaporated to an oil. This oil was purified by flash chromatography (silica, 5% ethyl acetate in DCM) to give 10 g product with 1H-pyrrol-1-amine. This was combined with 2 g product obtained from a previous condensation, triturated with petroleum ether and purified by high pressure liquid chromatography (HPLC hereafter) (silica, 10% ethyl acetate in DCM) to give 4.8 g of an oil. This oil was crystallized by triturating with hexane to give 4 g (44%) solid, m.p. 100° C. This solid was recrystallized from ether-hexane to give 3 g (33%) of 6-Chloro-$N^4$-(1H-pyrrol-1-yl)-4,5-pyrimidinediamine m.p. 130°-132°.

Analysis: Calculated for $C_8H_8ClN_5$: 45.83%C, 3.85%H, 33.41%N. Found: 45.71%C, 3.86%H, 33.16%N.

EXAMPLE 5

2-Chloro-N-methyl-N-(1H-pyrrol-1-yl)-4-pyrimidinamine

To 50 ml absolute ethanol, was added 2,4-dichloropyrimidine (5.0 g) and triethylamine (5.8 ml) followed by a solution of N-methyl-N-(1H-pyrrol-1-yl)amine (3.2 g) in 30 ml absolute ethanol.

After stirring at 80° C. for twenty hours, the mixture was poured into 60 ml water, stirred for fifteen minutes, and the resultant precipitate collected, washed with water, dissolved in ether, then dried over anhydrous $Na_2SO_4$.

After filtering, the solvent was evaporated to a solid, 4.0 g (56%), m.p. 72°-77° C.; which was sublimed at 90° C./1.0 mmHg to give 2.4 g (34%) of 2-Chloro-N-methyl-N-(1-H-pyrrol-1-yl)-4-pyrimidinamine, m.p. 102°-103° C.

Analysis: Calculated for $C_9H_9ClN_4$: 51.81%C, 4.35%H, 26.85%N. Found: 51.73%C, 4.34%H, 26.70%N.

EXAMPLE 6

N-Methyl-N-(1H-pyrrol-1-yl)-4-pyrimidinamine

6-Chloro-N-methyl-N-(1H-pyrrol-1-yl)-4-pyrimidinamine (7.2 g), in 200 ml of ethanol (100%) was hydrogenated under atmospheric pressure at room temperature in the presence of 10% Pd/C (2.0 g) and MgO (1.6 g). When the reaction was complete, the mixture was filtered through celite, and the filtrate evaporated to yield a solid (8.3 g) which was eluted with 10% ethyl acetate/DCM on a silica gel column via flash chromatography. The desired fractions were evaporated to yield 3.74 g (63.3%) of a solid, N-Methyl-N-(1H-pyrrol-1-yl)-4-pyrimidinamine, m.p. 97°-99° C.

Analysis: Calculated for $C_9H_{10}N_4$: 62.05%C, 5.79%H, 32.16%N. Found: 61.79%C, 5.74%H, 31.84%N.

EXAMPLE 7

6-Chloro-N-(1H-indol-1-yl)-4-pyrimidinamine

To 250 ml isopropanol, was added 4,6-dichloropyrimidine (12 g), 1 ml ethereal -HCl, and 1H-indol-1-amine (15 g). After stirring at 90° C. for seven hours, the mixture was poured into 300 ml iced water, stirred for five minutes, then extracted three times with 200 ml of ethyl acetate. The organic layer was washed with water, then dried (saturated NaCl, anhydrous $MgSO_4$).

After filtering, the solution was evaporated to an oil, approximately 25 g; which was eluted on a silica gel column with DCM via flash chromatography. The desired fractions were combined, then evaporated to a solid, 6.0 g (35%), 140° C. (dec.). A sample of this material, product 6-Chloro-N-(1H-indol-1-yl)-4-pyrimidinamine, was sublimed to a solid at about 135° C./1 mm Hg, m.p. 170°-171° C.

Analysis: Calculated for $C_{12}H_9ClN_4$: 58.91%C, 3.71%H, 22.90%N. Found: 59.02%C, 3.63%H, 22.71%N.

EXAMPLE 8

N-(1H-Indol-1-yl)-4-pyrimidinamine

To a suspension of 10% Pd/C (1.0 g) and MgO (0.8 g) in 100 ml ethanol, was added 6-chloro-N-(1H-indol-1-yl)-4-pyrimidinamine (3.5 g).

After stirring at ambient temperature under one atmosphere of $H_2$ for six hours, the mixture was filtered through celite and the filtrate evaporated to an oil, 4 g, which was eluted on a silica gel column with 5% ethyl acetate/DCM via HPLC. The desired fractions were combined, then evaporated to a solid, 2.6 g, m.p. 70°-75° C.

This material was sublimed at 110° C. @ 2 mm Hg to give 2.1 g solid of N-(1H-Indol-1-yl)-4-pyrimidinamine, m.p. 81°-85° C.

Analysis: Calculated for $C_{12}H_{10}N_4$: 68.56%C, 4.79%H, 26.65%N. Found: 68.40%C, 4.84%H, 26.29%N.

EXAMPLE 9 a. N-Propyl-1H-pyrrol-1-amine

To 1H-pyrrol-1-amine (82 g) in 500 ml of dichloromethane (DCM) was added $NaHCO_3$ (150 g) and this mixture was cooled to ice bath temperature. To this was added ethyl chloroformate (104 ml) dropwise, and the mixture was stirred at ice bath temperature for one hour, then at room temperature for four hours. The mixture was filtered and the filtrate was washed with water and dried (saturated NaCl, anhydrous $MgSO_4$). After filtering, the solvent was evaporated to yield a solid, 154 g (100%), m.p. 59°-61° C. This material was then dissolved in 500 ml of tetrahydrofuran (THF) and cooled to ice bath temperature. Potassium t-butoxide (139.13 g) was added portionwise, to the mixture and the reaction was stirred at ice bath temperature for one hour. A solution of iodopropane in 20 ml of THF was added dropwise, and the mixture was stirred at room temperature for five hours. The mixture was then poured into water and extracted twice with ethyl acetate. The combined organics were washed with water and dried (saturated NaCl, anhydrous $MgSO_4$). After filtering, the solvent was evaporated to yield an oil, 178.55 g (87.6%). This material was dissolved in ethylene glycol (250 ml) and to this was added NaOH (43.69 g) in 200 ml of $H_2O$. This mixture was heated to 120° C. and stirred vigorously for seven hours. The mixture was then poured into water and extracted three times with ethyl acetate. The combined organics were washed with water and dried (saturated NaCl, anhydrous $MgSO_4$). After filtering, the solvent was evaporated to yield an oil (158 g) which was distilled to yield an oil, 102 g (90%), of N-propyl-1H-pyrrol-1-amine.

b. 6-Chloro-N-propyl-N-(1H-pyrrol-1-yl)-4-pyrimidinamine

To 15 g of 4,6 dichloropyrimidine in 80 ml of ethanol (100%) was added 27.8 ml of triethylamine and N-propyl-1H-pyrrol-1-amine (12.4 g). This mixture was heated to reflux and stirred for 26 hours. After cooling, the mixture was poured into water and extracted with ethyl acetate. The organic layer was washed with water and dried (sat. NaCl, anhy. $MgSO_4$).

After filtering, the solvent was evaporated to yield 24.68 g of an oil which was eluted with DCM on a silica gel column via HPLC. The desired fractions were evaporated to yield 7.4 g of an oil. This material was distilled under vacuum to yield an oil, product 6-Chloro-N-propyl-N-(1H-pyrrol-1-yl)-4-pyrimidinamine, which solidified on standing, 2.15 g (10%), m.p. 52°-54° C.

Analysis: Calculated for $C_{11}H_{13}ClN_4$: 55.82%C, 5.54%H, 23.67%N. Found: 55.82%C, 5.53%H, 23.50%N.

EXAMPLE 10

N-(1H-Indol-1-yl)-N-propyl-4-pyrimidinamine

To 100 ml ethanol, was added 10% Pd/C (1.2 g), MgO (1.0 g), and 6-chloro-N-(1H-indol-1-yl)-N-propyl-4-pyrimidinamine (4.2 g). After stirring under $H_2$ at ambient temperature for three hours, the mixture was filtered, and the filtrate evaporated to 4.0 g of an oil. This material was eluted on a silica gel column with 10% ethyl acetate/DCM via HPLC, to give 2.4 g (66%) of an oil, product N-(1H-Indol-1-yl)-N-propyl-4-pyrimidinamine.

Analysis: Calculated for $C_{15}H_{16}N_4$: 71.40%C, 6.39%H, 22.20%N. Found: 71.14%C, 6.42%H, 21.89%N.

EXAMPLE 11 a. N-Propyl-1H-indol-1-amine

To a suspension of $NaHCO_3$ (50 g) in 100 ml dichloromethane (DCM) was added a solution of 1H-indol-1-amine (36 g) in 200 ml DCM. After cooling to 0° C. with an ice bath, a solution of ethyl chloroformate (29 ml) in 50 ml DCM was added over a period of thirty minutes. After stirring at ambient temperature for three hours, the mixture was filtered, and the filtrate washed with water, then dried (saturated NaCl, anhydrous $MgSO_4$). After filtering, the solvent was evaporated to an oil which was eluted on a silica gel column with DCM, via HPLC to give N-(1H-indol-1-yl) carbamic acid ethyl ester, 33.6 g (61%) as an oil. To a cold solution of N-(1H-indol-1-yl) carbamic acid ethyl ester (15 g) in 100 ml tetrahydrofuran, was added potassium t-butoxide (9 g) and the mixture stirred at 5° C. for one hour. To this was added 1-bromopropane (7.3 ml) and the mixture stirred at ambient temperature for five hours. The mixture was poured into 300 ml iced-water, stirred for five minutes, then extracted with ethyl acetate. The organic layer was washed with water, then dried (saturated, NaCl, anhydrous $MgSO_4$). After filtering, the solvent was evaporated to give N-(1H-indol-1-yl)-N-propylcarbamic acid ethyl ester as an oil, 16.5 g (91%). To a solution of N-(1H-indol-1-yl)-N-propylcarbamic acid ethyl ester (16.5 g) in 35 ml ethylene glycol, was added a solution of NaOH (10 g) in 30 ml water. After stirring at 120° C. for four hours, the mixture was poured into 300 ml ice water, stirred for five minutes, then extracted with ethyl acetate. The organic layer was washed with water, then dried (saturated NaCl, anhydrous $MgSO_4$). After filtering, the solvent was evaporated to give N-(1H-indol-1-yl)-N-propylamine, 9.0 g (78%) as an oil.

b. 6-Chloro-N-(1H-indol-1-yl)-N-propyl-4-pyrimidinamine

To 100 ml 1-methyl-2-pyrrolidinone, was added 4,6-dichloropyrimidine (10 g), followed by 1 ml ethereal -HCl and N-propyl-1H-indol-1-amine (12 g). After stirring at 120° C. for twenty-two hours, the mixture was cooled, poured into 500 ml water, stirred for five minutes, then extracted with ethyl ether. The organic layer was washed with water, then dried (saturated NaCl, anhydrous $MgSO_4$).

After filtering, the solvent was evaporated to 20 g of an oil, which was eluted on a silica gel column with DCM via HPLC, to give an oil, 9.2 g (46%), product 6-Chloro-N-(1H-indol-1-yl)-N-propyl-4-pyrimidinamine.

Analysis: Calculated for $C_{15}H_{15}ClN_4$: 62.83%C, 5.27%H, 19.54%N. Found: 63.12%C, 5.31%H, 19.41%N.

EXAMPLE 12 a. 3-Methyl-1H-indol-1-amine

To 700 ml of dimethylformamide (DMF) was dissolved 3-methyl indole (50 g) and the solution was cooled to 4° C. with an ice-salt bath. Milled KOH (121.8 g) was added to the mixture portionwise, keeping the internal temperature at 4° C. Hydroxylamine-O-sulfonic acid (56.54 g) was added portionwise over two hours, keeping the internal temperature between 4°-9° C. After the addition was complete, the reaction was stirred for one hour at about 9° C. The mixture was then poured into 1.4 l of ice-water to bring the total volume to 2.4 l. The aqueous layer was then extracted three times with ethyl acetate, the organics combined, washed with water and dried (saturated NaCl, anhydroux MgSO$_4$). After filtering, the solvent was evaporated to yield an oil (64.45 g) which was eluted with 50% hexanes in dichloromethane, and then dichloromethane. The desired fractions were evaporated to yield a solid of 3-methyl-1H-indol-1-amine, 32.4 g (58.4%) m.p. 60°-63° C.

b.
6-Chloro-N-(3-methyl-1H-indol-1-yl)-4-pyrimidinamine

To 125 ml of 1-methyl-2-pyrrolidinone was added 3-methyl-1H-indol-1-amine (10.0 g), and this mixture was heated to 120° C. Then 4,6-dichloropyrimidine (10.43 g), was added to the hot solution and this mixture was stirred for four hours. The reaction was cooled, poured into water, basified with Na$_2$CO$_3$ (aq) extracted with ethyl acetate and the organic layer washed with water and dried (sat. NaCl, anhy. MgSO$_4$).

After filtering, the solvent was evaporated to yield 25.75 g of an oil which was eluted with 5% ethyl acetate/DCM on a silica gel column via HPLC. The desired fractions were evaporated to yield 7.4 g of a solid. Of this material 4.0 g was eluted with ether/pet ether (1:1) on a silica gel column via flash method. The desired fractions were evaporated to yield 3.92 g of a solid. This material was recrystallized from ether/hexane (1:5) to yield 2.54 g (30%) of a solid, 6-Chloro-N-(3-methyl-1H-indol-1-yl)-4-pyrimidinamine, m.p. 159°-161° C.

Analysis: Calculated for C$_{13}$H$_{11}$ClN$_4$: 60.35%C, 4.29%H, 21.66%N. Found: 60.24%C, 4.30%H, 21.59%N.

EXAMPLE 13

N,N'-bis(1H-Indol-1-yl)-5-nitro-4,6-pyrimidinediamine

A solution of 4,6-dichloro-5-nitropyrimidine (8 g), and 1H-indol-1-amine (12 g), in 100 ml ethanol was warmed on a steam bath for thirty minutes then was cooled, diluted with ether and filtered to give 8 g of a solid, 250° (dec.). 4 g were purified by flash chromatography (silica/DCM) to give 3.5 g of a solid. This solid was recrystallized from acetone-ether to give 2.2 g (28%) of N,N'-bis(1H-Indol-1-yl)-5-nitro-4,6-pyrimidinediamine, 258°-260° (dec.).

Analysis: Calculated for C$_{20}$H$_{15}$N$_7$O$_2$: 62.33%C, 3.92%H, 25.44%N. Found: 62.13%C, 3.85%H, 25.50%N.

EXAMPLE 14

N-propyl-N-(1H-pyrrol-1-yl)-4-pyrimidinamine

To a slurry of 10% Pd/C (1.0 g) and MgO (0.8 g) in 10 ml ethanol (100%) was added 6-chloro-N-propyl-N-(1H-pyrrol-1-y)-4-pyrimidinamine (4.9 g), in 90 ml ethanol (100%) and the mixture was hydrogenated under atmospheric pressure at room temperature for 6 hours. The mixture was filtered and the filtrate evaporated to yield 4.92 g of a solid which was eluted with 10% ethyl acetate/DCM on a silica gel column via flash method. The desired fractions were evaporated to yield 2.45 g (57.8%) of an oil, N-propyl-N-(1H-pyrrol-1-yl)-4-pyrimidinamine.

Analysis: Calculated for C$_{11}$H$_{14}$N$_4$: 65.32%C, 6.98%H, 27.70%N. Found: 65.51%C, 6.99%H, 27.86%N.

EXAMPLE 15

N-(3-methyl-1H-indol-1-yl)-4-pyrimidinamine

To a slurry of 10% Pd/C (1.0 g) and MgO (0.8 g) in 10 ml ethanol (100%) was added 6-chloro-N-(3-methyl-1H-indol-1-yl)-4-pyrimidinamine (3.5 g), in 90 ml of ethanol (100%) and this mixture was hydrogenated under atmospheric pressure for 8 hours at room temperature. The mixture was then filtered and the filtrate evaporated to yield 3.92 g of a solid which was eluted with 10% ethyl acetate/DCM on a silica gel column via flash method. The desired fractions were evaporated to yield 2.0 g (63.8%) of N-(3-methyl-1H-indol-1-yl)-4-pyrimidinamine, as an oil which solidified on standing, m.p. 121°-123° C.

Analysis: Calculated for C$_{13}$H$_{12}$N$_4$: 69.62%C, 5.40%H, 24.98%N. Found: 69.69%C, 5.69%H, 25.39%N.

EXAMPLE 16

N,N'-bis(3-methyl-1H-indol-1-yl)-4,6-pyrimidinediamine

To 1-methyl-2-pyrrolidone (150 ml) was added 4,6-dichloropyrimidine (12.66 g), and 3-methyl-1H-indol-1-amine (12 g), and this mixture heated to 120° C. and stirred for 3 hours. The mixture was cooled, poured into water and extracted with ethyl acetate. The organic layer was washed with water and dried (sat. NaCl, anhy. MgSO$_4$).

After filtering, the solvent was evaporated to yield 22 g of an oil. This material was dissolved in 5% ethyl acetate/DCM and the insoluble material was collected to yield 5.0 g of a solid. This material was recrystallized from methanol to yield 1.6 g (5.3%) of a solid, N,N'-bis(3-methyl-1H-indol-1-yl)-4,6-pyrimidinediamine, m.p. 254°-256° C.

Analysis: Calculated for C$_{22}$H$_{20}$N$_6$: 71.72%C, 5.47%H, 22.81%N. Found: 71.59%C, 5.45%H, 22.69%N.

EXAMPLE 17

6-Chloro-N-(3-methyl-1H-indol-1-yl)-N-propyl-4-pyrimidinamine

To a suspension of NaH (60% in oil, 1.52 g) in 40 ml dimethylformamide (hereafter DMF) at ice bath temperature was added 9.0 g of 6-chloro-N-(3-methyl-1H-indol-1-yl)-4-pyrimidinamine dropwise, in 50 ml DMF. After addition was complete, the reaction was stirred for 5 minutes and then 3.45 ml of 1-bromopropane was added dropwise to the cool mixture. Reaction was allowed to proceed for 4 hours at room temperature. The mixture was then poured into water and extracted with ethyl acetate. The organic layer was washed with water and dried (sat. NaCl, anhy. MgSO$_4$).

After filtering, the solvent was evaporated to yield 10.0 g of a solid, which was eluted with DCM on a silica gel column via HPLC. The desired fractions were evaporated to yield 9.1 g (86.5%) of a solid, 6-Chloro-N-(3-methyl-1H-indol-1-yl)-N-propyl-4-pyrimidinamine, m.p. 99°-102° C.

Analysis: Calculated for $C_{16}H_{17}ClN_4$: 63.89%C, 5.70%H, 18.63%N. Found: 63.72%C, 5.65%H, 18.38%N.

EXAMPLE 18

N-(3-methyl-1H-indol-yl)-N-propyl-4-pyrimidinamine

To a slurry of 10% Pd/C (1.0 g) and MgO (0.8 g) in 20 ml of ethanol (100%) was added 4.5 g of 6-chloro-N-(3-methyl-1H-indol-1-yl)-N-propyl-4-pyrimidinamine in 50 ml of ethanol. This was hydrogenated under atmospheric pressure at room temperature. When the reaction was complete, the mixture was filtered and the filtrate evaporated to yield 5.2 g of a solid which was eluted with 5% ethyl acetate/DCM on a silica gel column via HPLC. The desired fractions were evaporated to yield 2.67 g (66.92%) of N-(3-methyl-1H-indol-1-yl)-N-propyl-4-pyrimidinamine, an oil which solidified on standing, m.p. 74°–76° C.

Analysis: Calculated for $C_{16}H_{18}N_4$: 72.15%C, 6.81%H, 21.04%N. Found: 72.21%C, 6.85%H, 21.02%N.

EXAMPLE 19

6-Chloro-$N^4$-(1H-indol-1-yl)-4,5-pyrimidinediamine

A solution of 8 g of 4,6-dichloro-5-pyrimidinamine, and 7 g of 1H-indol-1-amine, in 100 ml N-methyl-2-pyrrolidone was stirred at 130°–135° for seven hours, then cooled, stirred with water and extracted with ether. The organic extract was washed with water and saturated sodium chloride, dried (anhy. MgSO$_4$), filtered and evaporated to 16 g of a residue. This was purified by flash chromatography (silica, 5% ethyl acetate/DCM) to give 10 g solid. This was combined with product obtained from other condensations and purified by HPLC (silica 5% ethyl acetate/DCM) to give 7 g oil. This oil was crystallized from ether-petroleum ether to give 2.2 g solid, 6-Chloro-$N^4$-(1H-indol-1-yl)-4,5-pyrimidinediamine, m.p. 175°–176°.

Analysis: Calculated for $C_{12}H_{10}ClN_5$: 55.50%C, 3.88%H, 26.97%N. Found: 55.69%C, 3.93%H, 26.91%N.

EXAMPLE 20

5-Cyano-N-(1H-indol-1-yl)-4-pyrimidinamine

To 100 ml absolute ethanol, was added 5.0 g of 1H-indol-1-amine, 5.0 g of 4-chloro-5-cyanopyrimidine and 5 ml of triethylamine. After stirring at ambient temperature for 20 hours, the mixture was poured into 400 ml water, stirred for five minutes, then extracted with ethyl acetate. The organic layer was washed with water, then dried (saturated NaCl, anhydrous MgSO$_4$).

After filtering, the solvents were evaporated to 12 g of a semi-solid which was eluted on a silica gel column with 5% ethyl acetate/DCM via HPLC. The desired fractions were combined, then evaporated to 3.0 g of a solid, m.p. 65°–70° C. This material was eluted on a silica gel column with 2% ethyl acetate/DCM via HPLC to give 2.4 g (27%) of a solid, 5-Cyano-N-(1H-indol-1-yl)-4-pyrimidinamine, m.p. 130°–135° C.

Analysis: Calculated for $C_{13}H_9N_5$: 66.37%C, 3.86%H, 29.77%N. Found: 65.83%C, 3.75%H, 29.28%N.

EXAMPLE 21 a. 9H-carbazol-9-amine

Into 250 ml of dimethylformamide was dissolved 25 g of carbazole. This solution was cooled with an ice-salt bath and 42 g of potassium hydroxide was added portionwise. To this mixture was added hydroxylamine-O-sulfonic acid. After two hours the mixture was stirred with water and extracted with ethyl acetate. The organic extracts were washed with water and brine. After filtering the solvent was evaporated and the residue was eluted with 25% dichloromethane in hexane on a silica column to yield 9.5 g of a mixture of carbazole and 9H-carbazol-9-amine.

b. N-(6-Chloropyrimidin-4-yl)-9H-carbazol-9-amine

To 150 ml of 1-methyl-2-pyrrolidinone was added 10.0 g of 9H-carbazol-9-amine, and 8.2 g of 4,6-dichloropyrimidine, and the mixture was heated to 100° C. and stirred for eleven hours. The mixture was then poured into water and extracted with toluene. The organic layer was washed with water and dried (sat. NaCl, anhydrous MgSO$_4$).

After filtering, the solvent was evaporated to yield 16.1 g of an oil which was eluted with 10% ethyl acetate/DCM on a silica gel column via HPLC. The desired fractions were evaporated to yield 6.5 g of a solid. 3.0 g of this material was recrystallized from ethanol to yield 2.2 g (30%) of solid, N-(6-Chloropyrimidin-4-yl)-9H-carbazol-9-amine, m.p. 190°–192° C.

Analysis: Calculated for $C_{16}H_{11}ClN_7$: 65.20% C, 3.76% H, 19.01% N. Found: 65.05% C, 3.70% H, 18.97% N.

EXAMPLE 22

N-(Pyrimidin-4-yl)-9H-carbazol-9-amine

To a slurry of 10% Pd/C (1.0 g) and 0.8 g MgO in 5 ml of ethanol was added 4.0 g of N-(6-chloropyrimidin-4-yl)-9H-carbazol-9-amine in 12.0 ml of ethanol and the mixture was hydrogenated at atmospheric pressure at room temperature. When the reaction was complete, the mixture was filtered and the filtrate was evaporated to yield 6.2 g of an oil, which was preabsorbed on silica gel and eluted with 5% ethyl acetate/DCM on a silica gel column via the flash method. The desired fractions were evaporated to yield 2.4 g (61.5%) of a solid, N-(pyrimidin-4-yl)-9H-carbazol-9-amine, m.p. 177°–180° C.

Analysis: Calculated for $C_{16}H_{12}N_4$: 73.83% C, 4.65% H, 21.52% N. Found: 73.63% C, 4.65% H, 21.37% N.

EXAMPLE 23

5-Cyano-N-(1H-indol-1-yl)-N-propyl-4-pyrimidinamine

To 80 ml ethanol was added 6.8 g of N-propyl-1H-indol-1-amine, triethylamine (5.8 ml), and 5.4 g of 4-chloro-5-cyanopyrimidine.

After stirring at 90° for five hours, the mixture was poured into 200 ml water and stirred for five minutes. The pH was adjusted to 10 with Na$_2$CO$_3$ solution, then extracted with ethyl acetate. The organic layer was washed with water, then dried (saturated NaCl, anhydrous MgSO$_4$).

After filtering, the solvents were evaporated to an oil, 15 g; which was eluted on a silica gel column with 5% ethyl acetate/DCM via HPLC. The desired fractions were combined and evaporated to an oil (6.0 g). This oil was then eluted on a silica gel column with 1% ethyl acetate/DCM via HPLC; and the desired fractions were combined, then evaporated to a solid, 2.9 g, m.p. 112°–115° C. This material was recrystallized from ethyl ether to give 2.1 g (18%) of 5-Cyano-N-(1H-indol- 1-yl)-N-propyl-4-pyrimidinamine, a solid, m.p. 129°–130° C.

Analysis: Calculated for $C_{16}H_{15}N_5$: 69.27% C, 5.45% H, 25.60% N. Found: 69.19% C, 5.40% H, 24.90% N.

We claim:

1. A method of synthesizing a compound of the formula

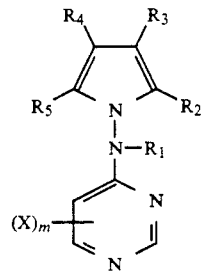

where $R_1$ is hydrogen, loweralkyl, aryl, or arylloweralkyl; $R_2$ and $R_3$ are independently hydrogen or loweralkyl, or $R_2$ and $R_3$ taken together are aryl; $R_4$ and $R_5$ are independently hydrogen or loweralkyl, or $R_4$ and $R_5$ taken together are aryl; X is hydrogen, halogen, cyano, nitro, amino, loweralkyl, loweralkoxy, trifluoromethyl or

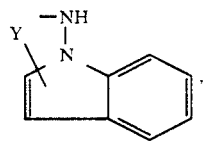

where Y is hydrogen, halogen or loweralkyl; m is an integer of 1 to 3; and the pharmaceutically acceptable acid addition salts thereof and where applicable the geometrical and optical isomers and racemic mixtures thereof which comprises reacting a

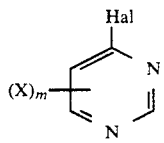

where Hal is halogen with a compound of the formula

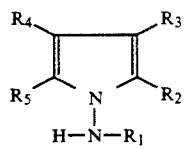

where $R_1$, $R_2$, $R_3$, $R_4$ and $R_5$ are as previously defined in a loweralkanol solvent or 1-methyl-2-pyrrolidinone.

2. A method of synthesizing a compound of the formula

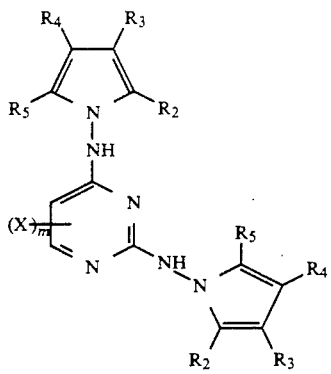

where $R_1$ is hydrogen, loweralkyl, aryl, or arylloweralkyl; $R_2$ and $R_3$ are independently hydrogen or loweralkyl, or $R_2$ and $R_3$ taken together are aryl; $R_4$ and $R_5$ are independently hydrogen or loweralkyl, or $R_4$ and $R_5$ taken together are aryl; X is hydrogen, halogen, cyano, nitro, amino, loweralkyl, loweralkoxy, trifluoromethyl or

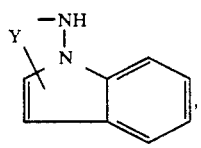

where Y is hydrogen, halogen or loweralkyl; m is an integer of 1 to 3; and the pharmaceutically acceptable acid addition salts thereof and where applicable the geometrical and optical isomers and racemic mixtures thereof which comprises reacting a compound of the formula

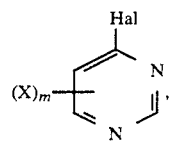

where Hal is halogen, with at least two moles of a compound of the formula

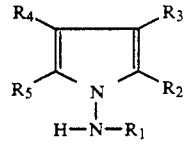

where $R_1$, $R_2$, $R_3$, $R_4$ and $R_5$ are as previously defined in a loweralkanol solvent or 1-methyl-2-pyrrolidinone.

* * * * *